(12) United States Patent
Tanaka (10) Patent No.: US 6,616,824 B1
(45) Date of Patent: Sep. 9, 2003

(54) APPARATUS FOR ELECTROPHORESIS (75) Inventor: Hiroshi Tanaka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/696,932

(22) Filed: Oct. 26, 2000

(30) Foreign Application Priority Data

Mar. 8, 2000 (JP) ......................................... 2000-063145

(51) Int. Cl.[7] ........................... C02F 1/40; C02F 11/00; C25B 11/00; C25B 13/00; C25B 9/00; G01N 27/27; G01N 27/403; G01N 27/453
(52) U.S. Cl. ...................................................... 204/603
(58) Field of Search ........................................ 204/603

(56) References Cited

U.S. PATENT DOCUMENTS

| | | | | |
|---|---|---|---|---|
| 5,784,157 A | * | 7/1998 | Gorfinkel et al. | 356/318 |
| 5,790,727 A | * | 8/1998 | Dhadwal et al. | 385/38 |
| 6,270,644 B1 | * | 8/2001 | Mathies et al. | 204/603 |
| 6,333,501 B1 | * | 12/2001 | Labrenz | 250/341.5 |
| 6,387,234 B1 | * | 5/2002 | Yeung et al. | 204/451 |
| 6,442,491 B1 | * | 8/2002 | Miller et al. | 702/19 |

* cited by examiner

Primary Examiner—Mark L. Bell
Assistant Examiner—Jennine Brown
(74) Attorney, Agent, or Firm—Beyer Weaver & Thomas LLP (57) ABSTRACT

An apparatus for electrophoresis includes not only a transparent device for electrophoresis such as a microchip or a capillary having a flow route, a power source for applying a voltage difference between end points of the flow route, an irradiating device for irradiating a specified portion of the flow route with light and an optical detector having a plurality of light-receiving elements arranged along the flow route for detecting absorption or emission of light by sample components separated in the flow route, but also a display device and a control unit for causing the display device to display data on the sample components separated in the flow route as a gel image based on detection signals from the optical detector while electrophoresis is being carried out by the apparatus. The gel image is for showing the sample components in a band form along the flow route, and the display device may also be adapted to display an electropherogram, showing absorptivity of light by or intensity of emitted light from the separated sample components along the flow route based also on the detection signals. Both the electropherogram and the gel image may show positions along the flow route in common.

13 Claims, 7 Drawing Sheets

POSITION ALONG FLOW ROUTE

FIG. 8C

APPARATUS FOR ELECTROPHORESIS

BACKGROUND OF THE INVENTION

This invention relates to an apparatus for electrophoresis for analyzing an extremely small amount of protein and nucleic acid. More particularly, the invention relates to an apparatus for electrophoresis using either a capillary or a microchip having a groove formed between a pair of transparent planar members and separating sample components therein by electrophoresis.

Apparatus for electrophoresis with a capillary have been largely in use for analyzing extremely small amounts of protein and nucleic acids. When such an apparatus with a capillary is used, a sample is injected from one end of the capillary and a voltage difference for electrophoresis is applied between the end points of the capillary to cause the sample to migrate inside.

Figure 1A:
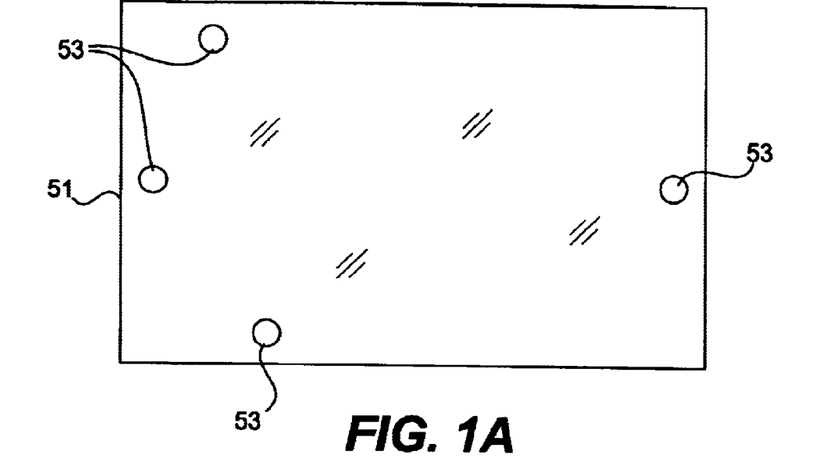
FIGS. 1A, 1B and 1C, together referred to as FIG. 1, show a microchip, FIGS. 1A and 1B being each a plan view of one of its base plates and FIG. 1C being its side view.
Figure 1B:
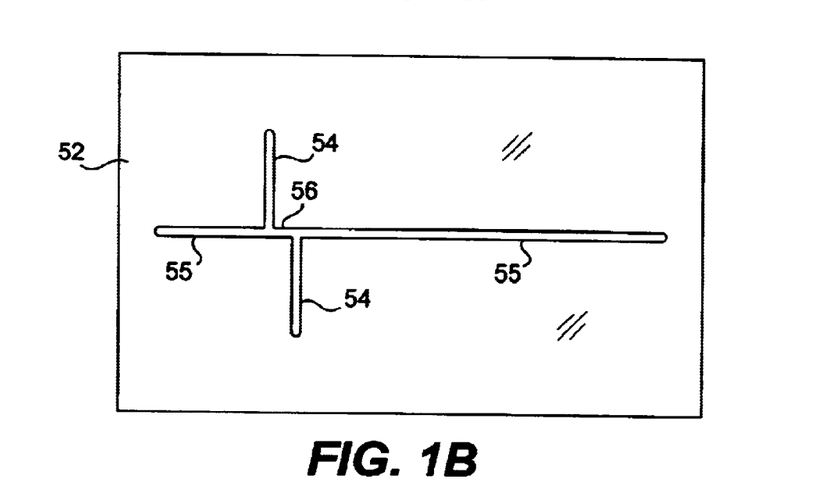
Figure 1C:
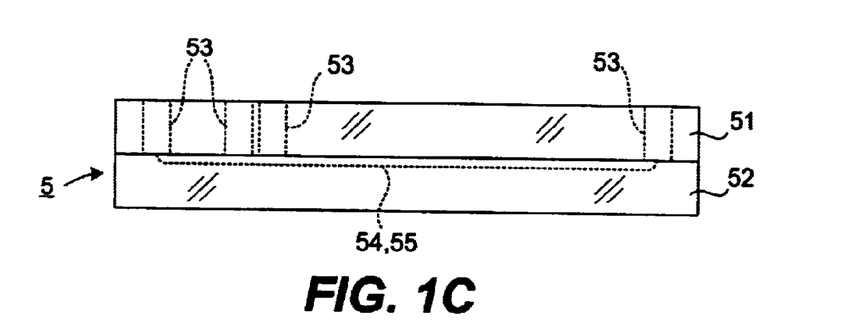

Recently, however, apparatus for electrophoresis having a microchip instead of a capillary are coming to be used. As shown in FIGS. 1A, 1B and 1C, a microchip 5 is formed by pasting together a pair of transparent base plates (the "upper plate 51" and the "lower plate 52"), say, made of a glass material. The lower plate 52 has mutually crossing capillary grooves (the "shorter groove 54" and the "longer groove" 55) formed on its surface for a migrating liquid to travel through, while the upper plate 51 has reservoirs 53 formed as throughholes at positions corresponding to the end points of the grooves 54 and 55.

The microchip 5 is formed by superposing the two base plates 51 and 52 as shown in FIG. 1C, and a liquid for electrophoresis is injected into the grooves 54 and 55 through any one of the reservoirs 53. Thereafter, a sample is injected into a reservoir 53 at either end of the shorter groove 54 and a high voltage is applied for a specified period of time between the ends of this groove 54 by inserting electrodes into the reservoirs 53 at both ends of the shorter groove 54. The sample is thereby caused to travel through the groove 54. Next, electrodes are inserted into the reservoirs 53 at both ends of the longer groove 55 and a voltage difference for electrophoresis is applied therebetween. This causes the portion of the sample at the crossing point 56 of the grooves 54 and 55 to migrate along the longer groove 55.

For detecting components of a sample, it has been a common practice to place a detector such as an ultraviolet/visible light spectrophotometer, a fluorescence photometer or an electrochemical detector along the flow route of the sample. Japanese Patent publication Tokkai 10-132783 has disclosed a different method of detection whereby a beam of light is made incident over a specified area along the flow route and an optical detector having a plurality of light-receiving elements disposed along the flow route is used to simultaneously detect the absorption or emission of light from the sample components separated inside the flow route over a specified range of distance therealong.

The migration pattern of sample components separated by an electrophoresis apparatus is usually displayed in the form of an electropherogram, showing absorption or intensity of emitted light by each component along the flow route for the separation. The pattern, however, may also be displayed as a gel image, showing the separated sample components as a band pattern along the flow route.

When the display is over a specified range of distance along the flow route for the separation, whether it is by way of an electropherogram or a gel image, the display is made as of a time by which the separation of the sample by electrophoresis has been completed. As long as the electrophoresis is carried out for the purpose of a quantitative analysis of protein or a nucleic acid, it is sufficient to display a pattern after the separation has been completed. According to a method of detection whereby a detector is placed at an appropriate position along the flow route for the separation for detecting the sample components as they pass, in particular, the sample components are displayed against a time axis and it is not a display of the entire migration pattern which changes constantly from one time to another along the flow route, although this is sometimes referred to as a real-time display.

Although an electropherogram and a gel image may both be displayed, not only is the display made after the separation by electrophoresis has been completed, but also the display is not made with the coordinate axes used in common. Such a display is not required if quantitative analysis is the only object.

It has been noted, however, that there are situations where it is desirable to ascertain the migration pattern not only after the separation has been completed but also during the course of the separation by electrophoresis. Such a situation comes about, for example, when the operator has noted an abnormal migration occurring between the start and the completion of electrophoresis. In such a situation, it is believed that the overall understanding of the migration pattern can be more easily obtained if the migration pattern during the course of migration is displayed as a gel image rather than as an electropherogram. It has never been done, however, to display the pattern during the course of migration as a gel image.

SUMMARY OF THE INVENTION

It is therefore an object of this invention, in view of the above, to provide an apparatus for electrophoresis capable of displaying a migration pattern during the course of migration of sample components as a gel image.

An apparatus for electrophoresis embodying this invention, with which the above and other objects can be accomplished, may be characterized as comprising not only a transparent device for electrophoresis such as a microchip or a capillary having a flow route, a power source for applying a voltage difference between end points of the flow route, an irradiating device for irradiating a specified portion of the flow route with light and an optical detector having a plurality of light-receiving elements arranged along the flow route for detecting absorption or emission of light by sample components separated in the flow route, but also a display device and a control unit for causing the display device to display data on the sample components separated in the flow route as a gel image based on detection signals from the optical detector while electrophoresis is being carried out by the apparatus. The gel image is for showing the sample components in a band form along the flow route, and the display device may also be adapted to display an electropherogram, showing absorptivity of light by or intensity of emitted light from the separated sample components along the flow route based also on the detection signals. Both the electropherogram and the gel image may show positions along the flow route in common.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings.

DETAILED DESCRIPTION OF THE INVENTION

Figure 2:
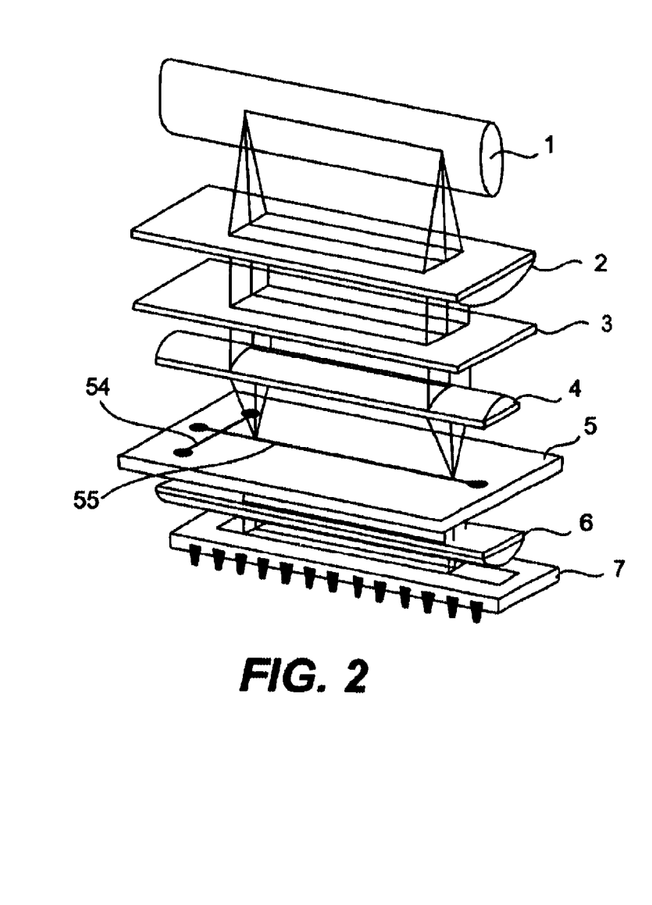
FIG. 2 is a schematic diagonal view of an apparatus embodying this invention.

The invention is described next by way of an example with reference to FIG. 2 wherein numeral 5 indicates the microchip explained above with reference to FIG. 1. In order to irradiate with light a specified region along its longer groove 55 serving as a flow path for separation of sample components, there is provided a light source 1 which is elongated linearly parallel to the groove 55. The light emitted from this linearly elongated light source 1 is passed through a cylindrical lens 2 to form a parallel beam and is made incident onto a band pass filter 3. After this parallel beam of light is passed through the band pass filter 3 and its wavelength is adjusted, it is converged by another cylindrical lens 4 along the flow route 55 through the microchip 5. On the opposite side of the microchip 5 is still another cylindrical lens 6 for converging the light which has passed through the flow route 55 and the light converged by this cylindrical lens 6 is made incident onto and detected by a photocell array 7 serving as a linear image sensor of an optical detector. The cylindrical lenses 2, 4 and 6, the band pass filter 3 and the photocell array 7 are each shorter than the flow route for the separation but nearly equal thereto in length.

The band pass filter 3 may be on the side of the microchip 5 towards the photocell array 7. A spectrograph comprising an element such as a prism or a diffraction grating may be substituted for the band pass filter. According to the example described above, the light from the light source 1 is made parallel by the cylindrical lens 2, only the portion of it having a specified wavelength is passed through the band path filter 3, the monochromatic beam of light thus obtained is converged onto the microchip 5 by means of the second cylindrical lens 4, and the light passing through the flow path through the microchip 5 is made parallel again by the third cylindrical lens 6 to be made incident onto the photocell array 7.

Figure 3:
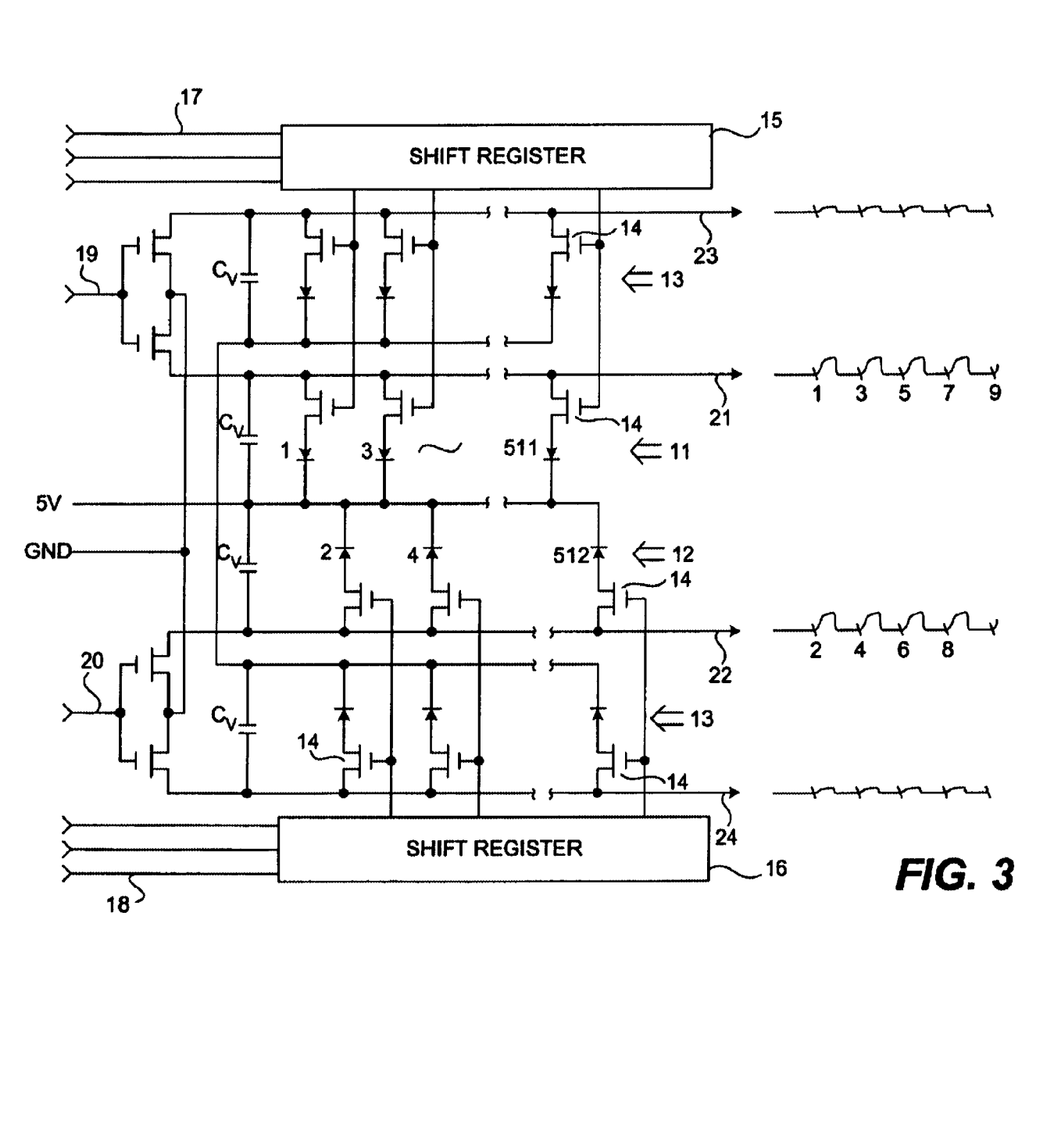
FIG. 3 is a circuit diagram of the photocell array of FIG. 2.

The invention does not impose any particular limitation on the structure of the photocell array 7. FIG. 3 shows the circuit structure of an example of the photocell array 7 having 512 sequentially aligned photodiodes arranged linearly on a straight line. For the convenience of description, those of the photodiodes at odd-numbered positions (that is, at the first, third, fifth positions, etc.) in the sequence will be hereinafter referred to as the odd-photodiodes 11 and those at the even-numbered positions (that is, at the second, fourth, sixth positions, etc.) will be hereinafter referred to as the even-photodiodes 12. Thus, the photocell array 7 has 256 odd-numbered photodiodes 11 and 256 even-numbered photodiodes. In addition, the photocell array 7 is provided with 512 dummy photodiodes 13 which have the same functional characteristics as the aforementioned odd-numbered and even-numbered photodiodes 11 and 12 but are so called because these dummy photodiodes 13 are not used in actual measurements. A switching element 14 comprising a MOS-FET is attached to each of these photodiodes 11, 12 and 13. Those of the switching elements 14 attached to the odd-numbered photodiodes 11 and a half of these 512 dummy photodiodes 13 are connected to a shift register 15 and those of the switching elements 14 attached to the even-numbered photodiodes 12 and the remaining half of these 512 dummy photodiodes 13 are connected to another shift register 16. Each switching element 14 is switched on and off by a signal received by a corresponding one of these shift registers 15 and 16. Numerals 17 and 18 each indicate an action signal input terminal respectively of these shift registers 15 and 16. Numerals 19 and 20 each indicate a reset signal input terminal associated respectively with the odd-numbered and even-numbered photodiodes 11 and 12. Numerals 21 and 22 each indicate an output terminal respectively for the odd-numbered and even-numbered photodiodes 11 and 12. Numerals 23 and 24 each indicate an output terminal for the dummy photodiodes 13. Symbols Cv each indicate a capacitor.

Figure 4:
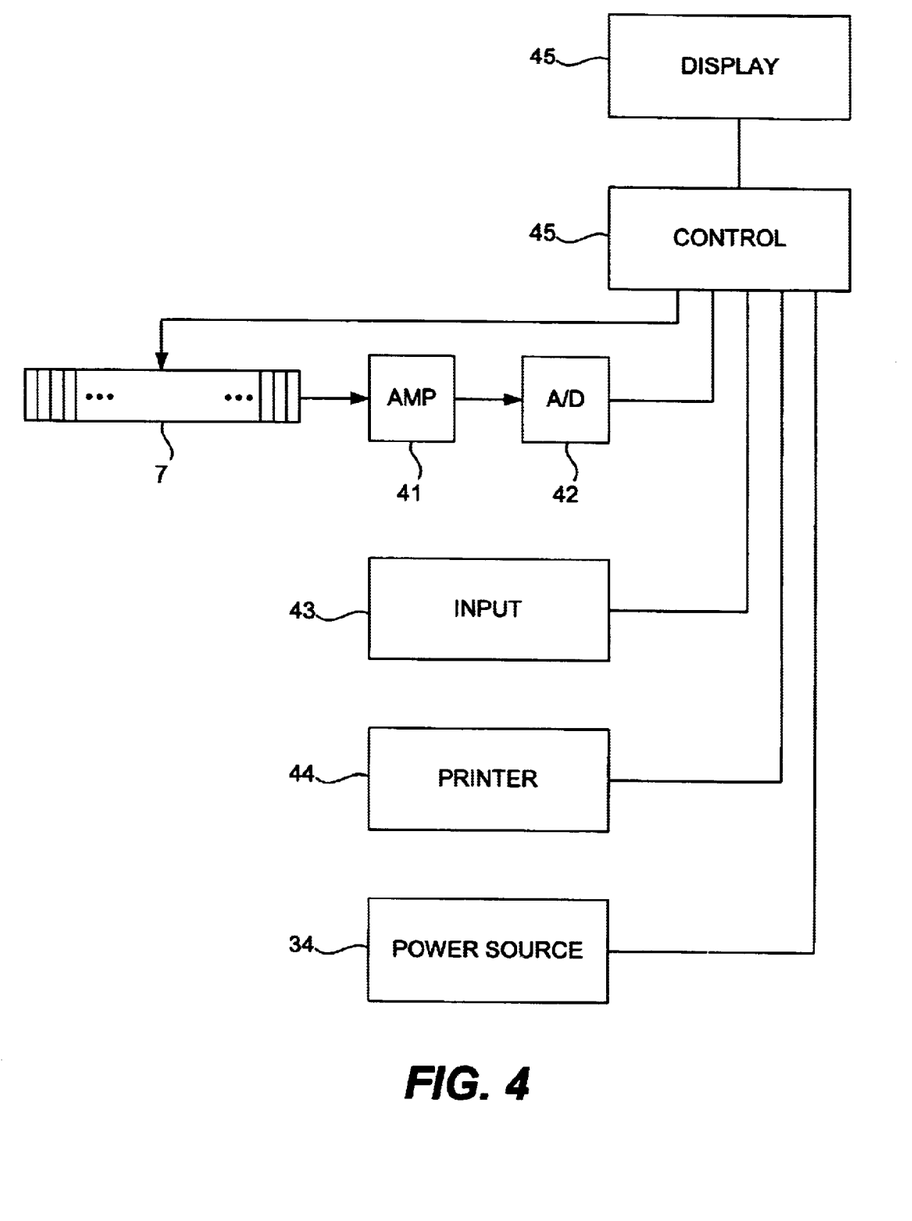
FIG. 4 is a block diagram of the control system for the apparatus of FIG. 2.

The apparatus for electrophoresis includes also a control unit 40 comprising a microcomputer including a CPU, a ROM and a RAM for its control and, as shown in FIG. 4, connected to the input terminals 17–20 of the photocell array 7. The output terminals 21–24 of the photocell array 7 are connected to the control unit 40 through an amplifier 41 and an A/D converter 42. The control unit 40 is also connected to an input device 43 with a keyboard through which an operator can input commands, a display device 45 such as a cathode ray tube (CRT) or a liquid crystal display plate, an XY printer 44 for outputting the results of measurement as charts, and a power source 34. The display device 45 serves to display a migration pattern during a migration process as a gel image together with or without an electropherogram or an electropherogram after the end of the migration process or the conditions and results of the analysis.

Figure 5:
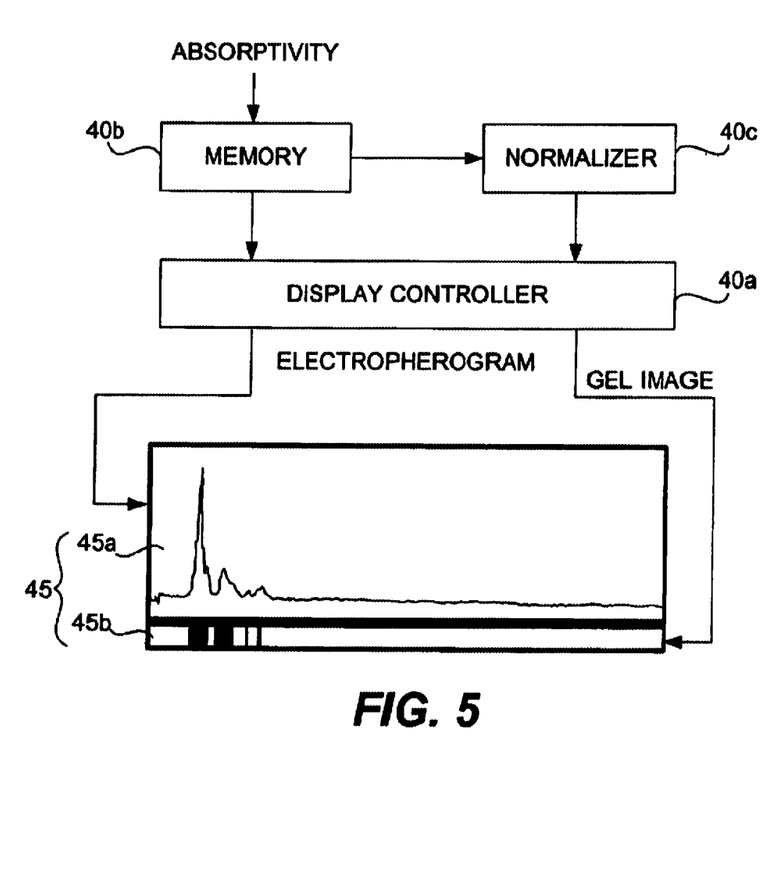
FIG. 5 is a block diagram for the display function of the control system of FIG. 4.

The function of the control unit 40 for displaying on the display device 45 a migration pattern during a migration process both as a gel image and as an electropherogram will be explained next with reference to FIG. 5. Let $Ir(n)$ indicate the quantity of light detected by the photoarray 7 before a sample is injected and let $Is(n,t)$ indicate the quantity of light during its separation process. Dummy index n indicates the position of detection, or the position of the light-receiving element of the photocell array 7 and dummy index t indicates the time after the beginning of the migration. From the detection signals obtained by the photocell array 7 and received through the amplifier 41 and the A/D converter 42, the control unit 40 calculates the absorptivity $Ab(n,t)$ at time t and position n as follows:

$$Ab(n,t) = -\log Is(n,t)/Ir(n)$$

where log is the common logarithm. The absorptivity $Ab(n,t)$ thus obtained is temporarily stored in a memory 40b. The maximum and minimum absorptivity values are obtained by a normalizer 40c over the entire detection region and these maximum and minimum values are used to normalize all the other absorptivity values into numbers between 0 and 1.

The control unit 40 further includes a display controller 40a which serves to display the normalized absorptivity value at each position by using a horizontal axis to indicate the positions and using different colors for different peaks to form a band-shaped gel image in a gel-image display area 45b of the display device 45. Different colors are specified for the individual peaks and the color density is adjusted between the densest color and the background color according to the normalized absorptivity value such that a display is made according to the magnitude of the absorptivity. The display controller 40a also serves to use the same horizontal axis for displaying an electropherogram in an electropherogram-display area 45a of the display device 45 and the absorptivity values corresponding to the individual positions.

Figure 6:
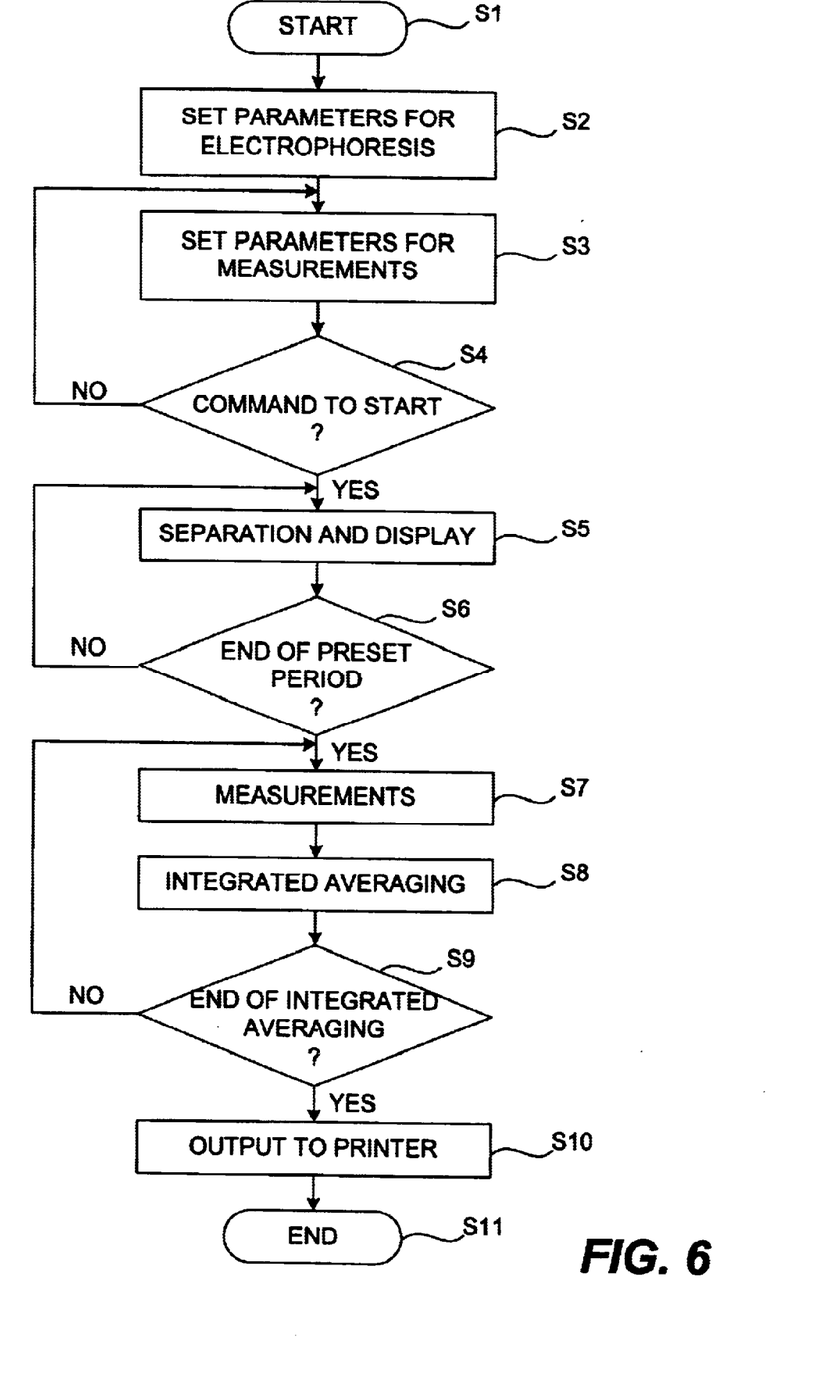
FIG. 6 is a flow chart of the operation of the apparatus of FIG. 2.

Operations of the control unit 40 for this example are described next with reference to the flow chart shown in FIG. 6. When its program is started, an initialization process is carried out (Step S1) which includes switching the power source 34 off and setting the printer 44 at its initial position. Next, the operator inputs through the input device 43 the time for injecting a sample, voltages to be applied and other parameters for the separation process (Step S2). After parameters related to the measurement such as the time to complete migration (which is the same as the time at which integrated averaging is started) and the time for carrying out the integrated averaging are also inputted by the operator (Step S3), the program enters a wait period for a command to start (Step S4).

After a sample is injected similarly as done in the case of prior art apparatus for electrophoresis, the operator presses a start button (not shown) on the keyboard. The electrophoretic separation of sample components is started according to the program and the inputted voltage difference is applied between the end points of the flow route inside the microchip 5. The sample becomes thereby separated into its components while migrating through the flow route.

Figure 7:
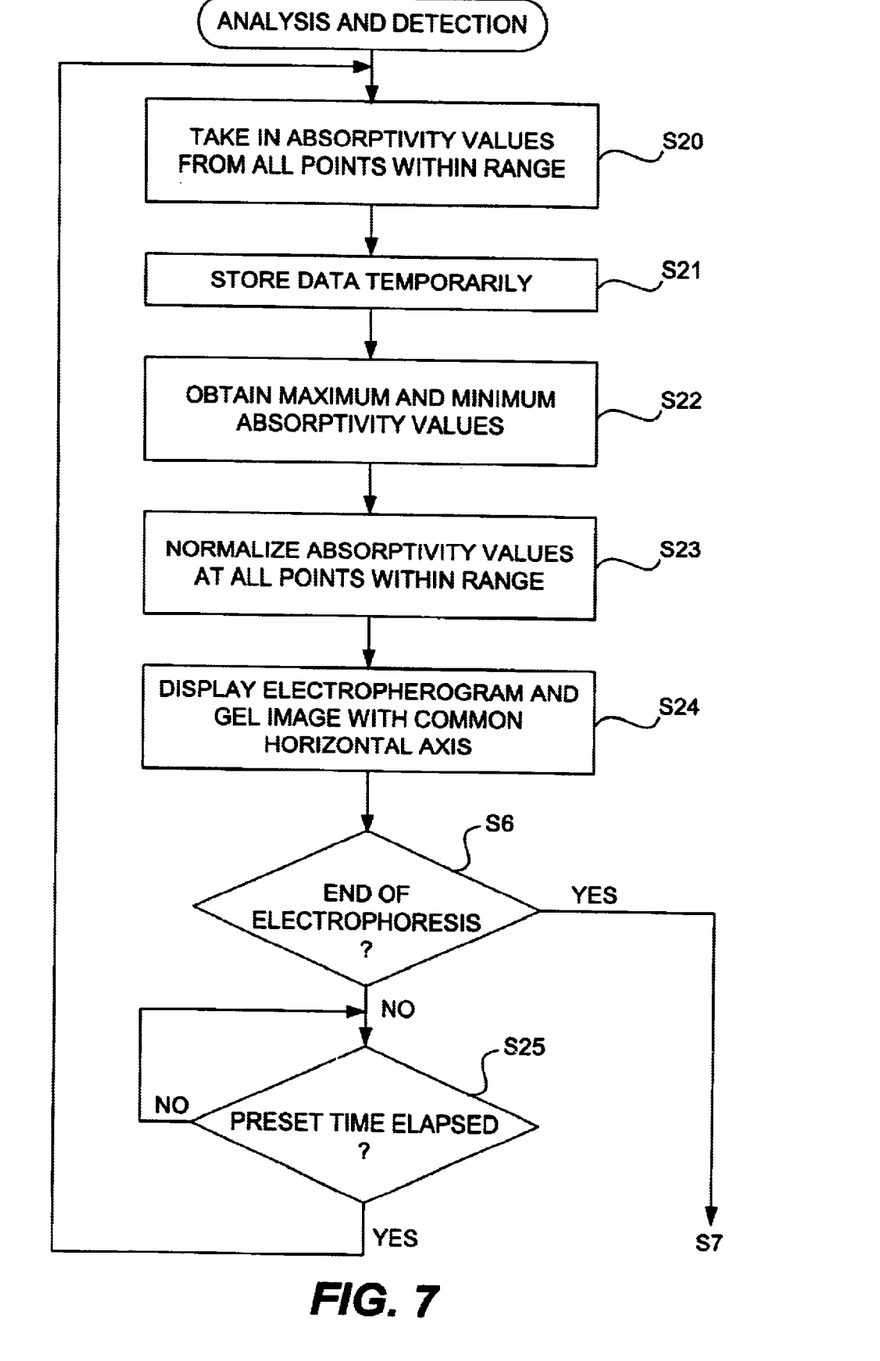
FIG. 7 is a flow chart related to the display operation by the control system.

As will be explained more in detail below with reference to FIG. 7, the conditions of separation by electrophoresis, after it is started, are displayed both as an electropherogram and as a gel image using the same horizontal axis in common as shown in FIG. 8, each of the photodiodes of the photocell array 7 corresponding to a different position along the flow route (Step S5). If the 512 photodiodes 11 and 12 of the photocell array 7 for measurement are arranged with a pitch of 25 $\mu$m, giving the photocell array 7 a total length of 12.8 mm, the absorptivity values over a portion of the flow route with length 12.8 mm can be thereby displayed with resolution of 25 $\mu$m. The electropherogram and the gel image are displayed accordingly.

At the end of the preset migration period (YES in Step S6), the sample components are in separated conditions inside the flow route. As a characteristic of electrophoresis either with the use of a capillary or a microchip, the separated components in the flow route remain separated, uninfluenced by the inertia force, as soon as the voltage difference for electrophoresis is switch off.

Measurements are started according to the parameters set in Step S3 (Step S7). The control unit 40 serves to repeatedly scan the photocell array 7 and, as the integrated averaging is repeated, the S/N ratio becomes steadily larger (Steps S7 and S8). At the end of the integrated averaging process (YES in Step S9), the results of the measurement are outputted to the printer (Step S10) and the program comes to its end (Step S11). The operations after the electrophoresis are explained more in detail in aforementioned Japanese Patent Publication Tokkai 10-132783.

The process of Step S6 for displaying the conditions of separation during electrophoresis both as an electropherogram and as a gel image using the same horizontal axis in common will be explained next more in detail by way of an example with reference to the flow chart shown in FIG. 7.

After the absorptivity values at all positions within the detection range are taken into the control unit 40 on the basis of the light intensities detected by the photocell array 7 (Step S20), these data are temporarily stored in its memory 40b (Step S21). Thereafter, a maximum value and a minimum value of absorptivity are ascertained (Step S22) and the absorptivity values at all positions are normalized to numbers between 0 and 1 (Step S23). After these normalized numbers are obtained, an electropherogram and a gel image are displayed on the display device 45 by using the same horizontal axis in common (Step S24). The series of operations from the calculation of the absorptivity values to the display is repeated periodically at constant time intervals until the end of electrophoresis (Steps S6 and S25).

Figure 8A:
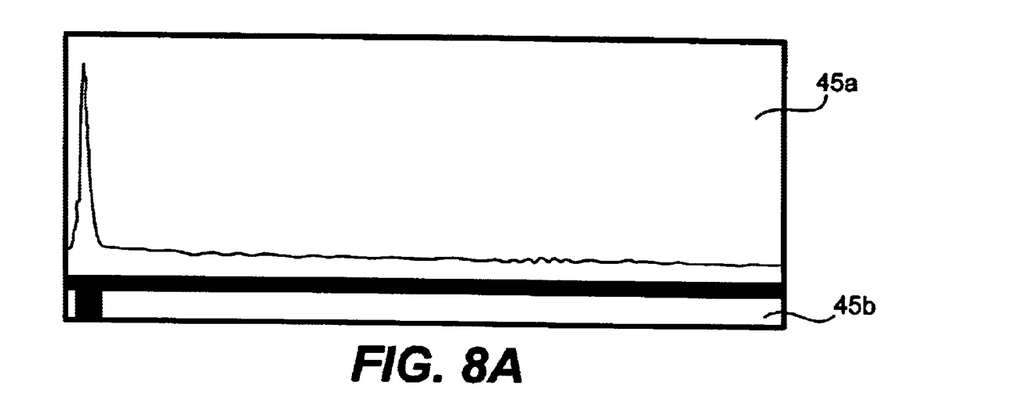
FIGS. 8A, 8B and 8C are an example of displays which change with time.
Figure 8B:
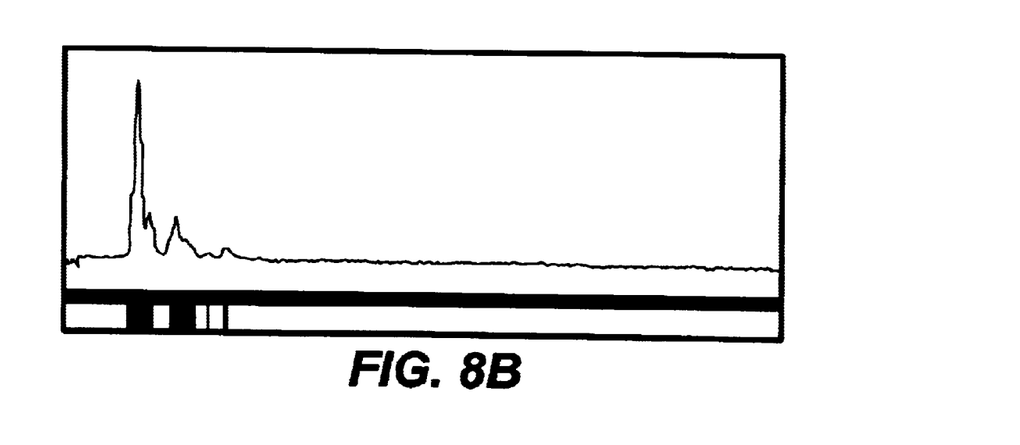
Figure 8C:
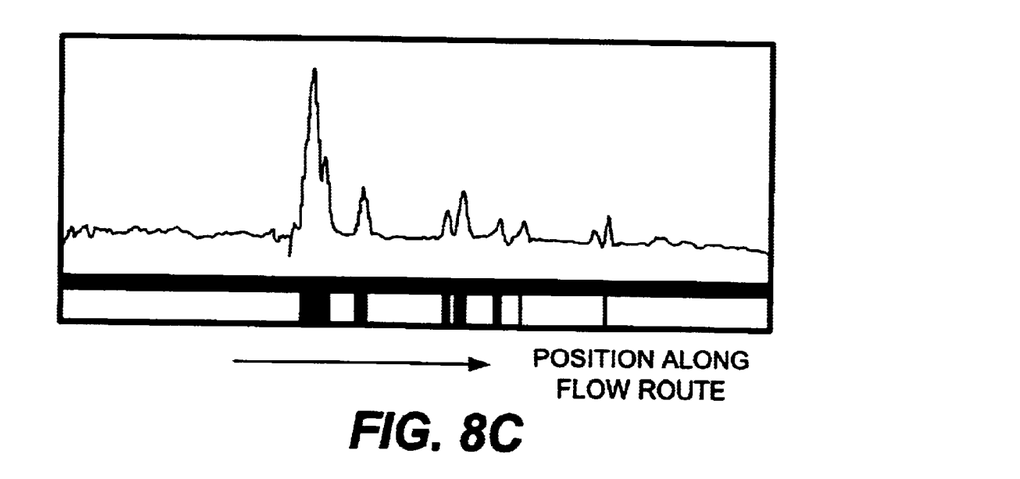

FIGS. 8A, 8B and 8C are examples of electropherogram and gel image displayed on the display device 45 at three different times in this order. The horizontal axes represent positions along the flow route for the separation, or the positions of the elements of the photocell array 7. In each of the graphs, the upper side is the electropherogram showing the absorptivity values and the lower side is the gel image showing the separated sample components in a band form. Such displays are made from the beginning of the electrophoresis in real time.

The method of gel image display may be varied in many ways in order to make it easier to read. If absorptivity is less than a certain threshold value, it may be treated as a part of the background and no display may be made such that the noise does not appear. If the baseline is adjusted to be straight, a more correct display of the gel image may be possible. The gel image can be made easier to read also if the color gradation is made not by linear interpolation but by using a non-linear function. A still another way to make the gel image easier to read is by not displaying absorption bands with less than a specified minimum width.

The invention has been described above with reference to only one example but many modifications and variations are possible within the scope of the invention. Although a routine for simultaneous display of an electropherogram and a gel image was described, the control unit may be so programmed that only a gel image will be displayed during the electrophoresis.

What is claimed is:
1. An apparatus for electrophoresis comprising:
   a device for electrophoresis comprising a transparent material and having formed therein a flow route in which sample components are separated;
   a power source for applying a voltage difference along said flow route;
   an irradiating device for irradiating a linearly elongated portion parallel to said flow route with light;
   an optical detector having a plurality of light-receiving elements arranged along said flow route for detecting absorption or emission of light by the sample components separated in said flow route;
   a display device; and
   a control unit for causing said display device to display data on the sample components separated in said flow route as a gel image based on detection signals from said optical detector while electrophoresis is being carried out by said apparatus, said gel image showing said sample components in a band form along said flow route.

2. The apparatus of claim 1 wherein said control unit also serves to cause said display device to display an electropherogram which shows absorptivity of light by or intensity of emitted light from said separated sample components along said flow route based on said detection signals, said electropherogram and said gel image showing positions along said flow route in common.

3. The apparatus of claim 1 wherein said device for electrophoresis comprises a microchip.

4. The apparatus of claim 2 wherein said device for electrophoresis comprises a microchip.

5. The apparatus of claim 1 wherein said device for electrophoresis comprises a capillary.

6. The apparatus of claim 2 wherein said device for electrophoresis comprises a capillary.

7. The apparatus of claim 1 wherein said control unit causes each color in a multicolor species to be displayed by a corresponding color on said display device.

8. The apparatus of claim 1 wherein said control unit also serves to carry out integrated averaging of the detection signals.

9. The apparatus of claim 2 wherein said control unit also serves to carry out integrated averaging of the detection signals.

10. The apparatus of claim 2 wherein said control unit also serves to calculate the absorptivity along said flow route, to obtain maximum and minimum values of the absorptivity, and to normalize the absorptivity into a number between 0 and 1 by using said maximum and minimum values.

11. The apparatus of claim 2 wherein said control unit is programmed so as not to display any absorption band with a width less than a preset minimum width.

12. The apparatus of claim 10 wherein said control unit is programmed so as not to display any absorption band with a width less than a preset minimum width.

13. The apparatus of claim 2 wherein said control unit is programmed so as not to display any absorptivity less than a preset threshold value.

* * * * *

UNITED STATES PATENT AND TRADEMARK OFFICE
CERTIFICATE OF CORRECTION

PATENT NO.    : 6,616,824 B1
DATED         : September 9, 2003
INVENTOR(S)   : Hiroshi Tanaka It is certified that error appears in the above-identified patent and that said Letters Patent is hereby corrected as shown below:

<u>Title page,</u>
Item [*] Notice, change "0 days" to -- 372 days --.

Signed and Sealed this

Twenty-third Day of December, 2003

JAMES E. ROGAN
*Director of the United States Patent and Trademark Office*